United States Patent [19]

Lim et al.

[11] Patent Number: 4,590,301

[45] Date of Patent: May 20, 1986

[54] POLYMERIZATION INHIBITORS

[75] Inventors: Drahoslav Lim; Peter C. Morris, both of San Diego, Calif.

[73] Assignee: Barnes-Hind, Inc., Sunnyvale, Calif.

[21] Appl. No.: 664,282

[22] Filed: Oct. 24, 1984

[51] Int. Cl.$^4$ ............... C07C 43/01; C07C 43/02; C07C 39/12; C07C 50/00
[52] U.S. Cl. ............... 568/633; 260/396 R; 560/56; 560/57; 560/61; 568/632; 568/640; 568/731; 568/732; 568/743; 568/744; 568/747
[58] Field of Search .............. 568/731, 732, 743, 744, 568/747, 632, 633, 640; 560/56, 57, 61; 260/396 R

[56] References Cited

U.S. PATENT DOCUMENTS

| | | | |
|---|---|---|---|
| 2,455,746 | 12/1948 | Erickson | 568/731 X |
| 3,424,821 | 1/1969 | Hunter | 568/731 X |
| 3,481,990 | 12/1969 | Hay | 568/732 |
| 4,094,857 | 6/1978 | Wolfe Jr. | 549/253 X |
| 4,324,925 | 4/1982 | Jupe et al. | 568/731 X |
| 4,446,264 | 5/1984 | Coffman | 549/253 X |
| 4,460,678 | 7/1984 | Yu et al. | 430/495 X |

FOREIGN PATENT DOCUMENTS 0635087 12/1978 U.S.S.R. ............... 568/731

OTHER PUBLICATIONS

"The Chemistry of the Quinonoid Compounds Parts 1 and 2", ed. Sam Patai, John Wiley & Sons, 1974.
"Basic Principles of Organic Chemistry", by Roberts and Caserio, W. A. Benjamin Inc., 1965.

Primary Examiner—John E. Kittle
Assistant Examiner—Mukund J. Shah

[57] ABSTRACT

Compounds of the general formula

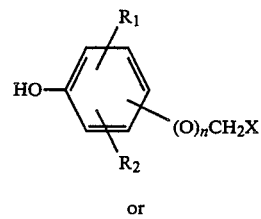

or

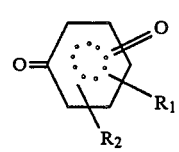

wherein n, $R_1$, $R_2$ and X are defined herein, are effective inhibitors of polymerization of vinylic monomers, particularly acrylic monomers. The inhibitors are easily, efficiently, and thoroughly removed from solution with the monomer by contact with charcoal.

34 Claims, No Drawings

POLYMERIZATION INHIBITORS

BACKGROUND OF THE INVENTION

The present invention relates to polymerization inhibitors and their removal from monomers.

Since monomers are by nature reactive, it is conventional practice to add a polymerization inhibitor to prevent unwanted, premature polymerization while the monomer is being stored or transported. Hydroquinone and hydroquinone-monomethyl ether are two inhibitors used for this purpose. While the inhibitors thus perform a valuable function, their very usefulness requires that they be removed from the monomer when the user wishes to polymerize the monomer. Conventional techniques for removing the inhibitor (distillation, crystallization, washing, solid adsorbtion) can be destructive to the monomer, or inefficient, and generally must be tailor-made based on the exact composition of the inhibitor, the monomer, and the solvent in which the monomer is dissolved. It is desirable to be able to remove inhibitors quickly in high yield, using inexpensive materials and minimizing the use of even those materials. To this end, the present inventors have discovered new and effective inhibitors which can be removed simply and efficiently from monomer-solvent systems.

SUMMARY OF THE INVENTION

The invention comprises compounds having the general formula (1) or (2):

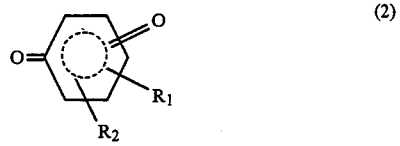

wherein
n is 0 or 1;
$R_1$ and $R_2$ are independently H, —OH, $C_1$–$C_6$ alkyl, X is
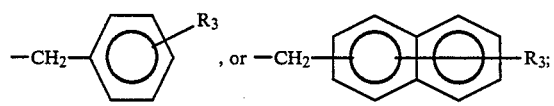

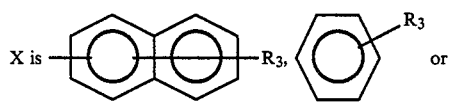

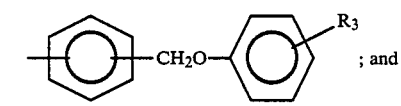
; and $R_3$ is H, —OH, —COO—($C_1$–$C_6$ alkyl), $C_1$–$C_6$ alkyl, or $C_1$–$C_6$ alkoxy, provided that the compound has at least three rings. The above notation is intended to show that in two-ring substituents $R_3$ can be attached to either ring. In formula (2), the ring contains two C=O groups and includes two C=C bonds.

The invention further comprises a stabilized monomer composition comprising a monomer having a vinylic bond, and at least one compound of formula (1) or (2) above present in an amount up to about 0.01 moles per mole of the monomer.

The invention comprises in another embodiment a method for inhibiting polymerization of a monomer having a vinylic bond, by adding to the monomer up to about 0.01 moles of an inhibitor of formula (1) or (2) above per mole of monomer.

A further embodiment of the invention comprises a method for removing an inhibitor of formula (1) or (2) from solution with a monomer, by contacting the monomer-inhibitor solution with an amount of charcoal effective to adsorb the inhibitor from the solution.

DETAILED DESCRIPTION OF THE INVENTION

The present invention relates to inhibitors of the formula (1) or (2) given above. The inhibitors within this formula include compounds having three rings (counting a naphthalene substituent, of course, as two rings). More preferred are compounds in which n equals 1, or $R_1$ is hydroxy, or both. In many preferred compounds of formula (1), either $R_1$ or the $(O)_n CH_2 X$ substituent is para to a hydroxyl group. Preferred alkyl groups include methyl and tertiary butyl. Preferred alkoxy groups include methoxy. Examples of compounds of this invention include:

| Compound | Melting Point, °C. |
| --- | --- |
| p-(naphthyl-1-methoxy)phenol | 121–122 |
| p-(naphthyl-2-methoxy)phenol | 177–178 |
| 2-(naphthyl-1-methyl)hydroquinone | 153–154 |
| 2-(naphthyl-1-methyl)-1,4-benzoquinone | 88–90 |
| o-xylylene-bis-hydroquinone ether | 158–160 |
| m-xylylene-bis-hydroquinone ether | 154–155 |
| p-xylylene-bis-hydroquinone ether | 216–218 |
| hydroquinone(4-phenoxymethyl)benzyl ether | 173–174 |
| 2,5-bis(Naphthyl-1-methyl)hydroquinone | 203–205 |
| 1-(3,4-dihydroxybenzyl)naphthalene | 108–109 |

Other compounds within this invention include: 2,5-dibenzylhydroquinone; 4-benzyloxy-2-benzylphenol; 2,5-dibenzyl-1,4-benzoquinone; 3-(naphthyl-1-methyl)-1, 2-benzoquinone, and 2,6-di-t-butyl-4-(naphthyl-1-methoxy)phenol.

The inventive compounds can readily be synthesized employing straightforward chemical practice. For instance, compounds of formula (1) in which n equals one can readily be made by reacting hydroquinone having substituents $R_1$ and $R_2$ as defined herein with a halo derivative under alkaline conditions employing a polar aprotic reaction solvent. The halo derivative is preferably a bromo and more preferably a chloro derivative. The aprotic solvent is preferably dimethylformamide. An example of such a preparation is given in example 4.

In practice the substituted 1,4 and 1,2 benzoquinones comprising formula (2) can be prepared by the oxidation of compounds of formula (1) in which n=0 and $R_1$=OH and the two hydroxy groups are para or ortho substituted. Example 5 is an illustration of this type preparation.

Compounds of formula (1) in which n=O and $R_1$=OH can be synthesized by reacting a dihydroxy benzene with a halo derivative in protic solvents. The halo derivative is preferably a bromo and more preferably a chloro derivative. The preferred solvent is ethyl alcohol. Example 6 gives such a synthesis.

Other synthetic routes for compounds of this invention will be readily apparent to the skilled chemist.

The inventive compounds are particularly useful as polymerization inhibitors for monomers having vinylic unsaturation, e.g. a C=C bond, such as styrene, divinylbenzene, chloromethylstyrene, isoprene, vinyl chloride, vinylacetate, vinylidene chloride, N-vinylpyrrolidone, and the like. The invention is particularly applicable to acrylic monofunctional and multifunctional monomers. Particularly preferred examples include acrylic acid, acrylamide, acrylonitrile, methacrylic acid, methyl methacrylate, octadecyl methacrylate, phenyl methacrylate, 2-hydroxyethyl methacrylate, 2,3-dihydroxypropyl methacrylate, methoxy triethyleneoxy methacrylate, heptafluorobutyl methacrylate, 3-methacryloxypropyl tris(trimethylsiloxy) silane, ethylene glycol dimethacrylate, neopentyl glycol diacrylate, polyoxyethylene dimethacrylate, pentaerythritol tetramethacrylate, and the like.

The inhibitor is used by simply dissolving the inhibitor in the monomer. Alternatively, the monomer and the inhibitor are dissolved in a co-solvent such as a hydrocarbon, ether, or alcohol, in which both are soluble. The latter case is especially applicable to solid monomers where a solution may be maintained or coprecipitation of a monomer inhibitor system effected. The amount of inhibitor should be effective to inhibit polymerization of the monomer under normal storage conditions. Generally, concentrations of up to about 0.01 mole percent can be employed, although amounts of about 0.001 to 0.005 mole per cent are highly satisfactory.

Polymerization is considered to be "inhibited" if it is less likely to occur, or if it occurs to a lesser degree compared to the monomer with no inhibitor or with a less effective inhibitor; and preferably polymerization does not occur at all.

The inhibitors can readily be removed from solution with the monomer by adsorption onto charcoal. This feature is a significant advantage of the present invention over previous inhibitor systems. Furthermore, the amount of charcoal needed to remove a given quantity of inhibitor is unexpectedly low compared to other inhibitors, and a lower final concentration of inhibitor can be reached more quickly. The inventive inhibitor can be removed by passing the monomer-inhibitor solution through a packed column of granulated charcoal. Alternatively, powdered charcoal can be stirred into the solution, and then filtered out. The contact time, and the surface area of the charcoal, are not critical but should be high enough to permit the desired adsorption to occur. For a given initial concentration of inhibitor, the amount of charcoal needed to achieve a given final concentration of inhibitor can readily be determined by those of ordinary skill in this art. The ease of removal is not materially affected by the choice of monomer, although the monomer preferably should have no more than one aromatic ring.

Thus, the present invention provides inhibitors which are useful for a wide choice of monomer, which are soluble in the monomer to a high enough degree to provide effective inhibition, and yet are easily and efficiently removable from the monomer. The invention is described further in the following examples.

EXAMPLE 1

A solution of 5400 g of 2-hydroxyethyl methacrylate ("HEMA") and 310 ppm of p-(naphthyl-1-methoxy)-phenol ("NMHQ"), an inhibitor within the scope of this invention, was passed through a 1-inch column of 150 g of granulated charcoal (Calgon CPG) at about 300 g of solution per hour. The inhibitor was removed to a final concentration of less than 4 ppm, even in the last portion of the solution to emerge from the column.

By comparison, when a solution of 5400 g of HEMA and 250 ppm of p-benzyloxyphenol ("BZHQ") was passed through an identical bed at 150 g/hour, the inhibitor concentration of the effluent rose above 4 ppm after only 1050 g of solution had passed through the column. In another comparison, when a solution of 5400 g of HEMA and 150 ppm of hydroquinone monomethyl ether ("MEHQ") was passed through an identical column at 30 g/hour, the inhibitor concentration of the effluent rose above 4 ppm after only 120 g of HEMA had passed through the column. In both of these comparative cases the inhibitor concentration continued to rise with continued elution. This comparison indicates that the new inhibitor, and solutions of the acrylic monomer and the inhibitor, exhibit significant improvement in the ease and thoroughness with which the inhibitor can be removed from the monomer.

EXAMPLE 2

The amount of granulated charcoal needed to lower the concentration of meta-xylylene-bis-hydroquinone ether ("m-XBHQ"), an inhibitor within the scope of this invention, from a starting concentration of 0.001 molar (320 ppm) in 200 ml of HEMA was determined by adding gradual amounts of charcoal, stirring about 16 hours to ensure that equilibrium was reached, and measuring the concentration of inhibitor remaining in solution. An inhibitor concentration of 25 ppm was reached when a total of 2.0 g of charcoal had been added. The concentration dropped to 9 ppm when a total of 4.0 g of charcoal had been added. The concentration dropped to 2 ppm when a total of 6.0 g of charcoal had been added.

EXAMPLE 3

In parallel runs, 6.0 g of charcoal was added to 200 ml test solutions of HEMA each of which was 0.001 molar in one of the four inhibitors listed in the Table below. After stirring to reach equilibrium, the concentrations of inhibitor were then measured.

TABLE

| Inhibitor | Initial Concn. (ppm) | Final Concn. (ppm) | % Reduction |
|---|---|---|---|
| MEHQ | 120 | 98 | 19.3 |
| BZHQ | 200 | 58 | 71.0 |
| NMHQ | 250 | 4 | 98.4 |
| m-XBHQ | 320 | 2 | 99.4 |

EXAMPLE 4

500 g hydroquinone was dissolved in 900 ml DMF and heated to 80° C., then 120 g of 50% concentrated sodium hydroxide was added. To this solution was added 250 g of 1-chloromethyl naphthalene over 6 hours. Reaction was heated at 80° C. for an additional 16 hours. The undesired hydroquinone diether precipitate was filtered off and the hydroquinone monoether was crystallized out of solution by addition of 500 ml water and cooling. The product was further purified by recrystallization from methanol/water. 200 g of p-(naphthyl-1-methoxy) phenol were obtained, melting range of the white crystals was 119°–121° C.

EXAMPLE 5

50 g 2-(naphthyl-1-methyl) hydroquinone was dissolved in 400 ml acetic acid with 25 g of Chromium VI oxide and heated at 40° C. for 1 hour. The red to green color shift of Cr VI to Cr III was apparent. The product was isolated from the ether phase of an ether/water liquid extraction of the reaction. 40 g of 2-(naphthyl-1-methyl)-1,4-benzoquinone was recovered, melting range of the orange crystals 88°–90° C.

EXAMPLE 6

40 g of Catechol and 25 g of 1-chloromethyl naphthalene were dissolved in 100 ml of ethanol and refluxed for 24 hours. The completed reaction mixture was diluted into 500 ml of water and the product was separated as an insoluble oil. The oil was then vacuum distilled at 0.1 mm Hg and the product boiling at 190°–200° C. was collected. The product was further crystallized from hexanes to yield 18 g colorless crystals of 1-(3,4-dihydroxybenzyl) naphthalene melting at 108°–109° C.

What is claimed is:

1. A compound having the formula (1) or (2):

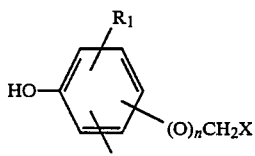

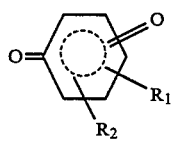

wherein
n is 0 or 1;
$R_1$ and $R_2$ are independently H, —OH, $C_1$–$C_6$ alkyl,

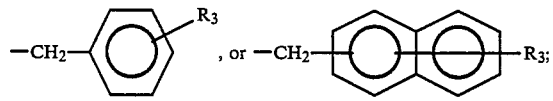

X is 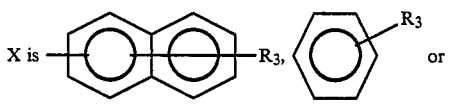

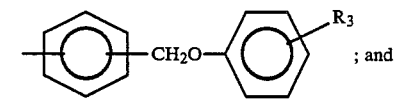

$R_3$ is H, —OH, —COO—($C_1$–$C_6$ alkyl), $C_1$–$C_6$ alkyl, or $C_1$–$C_6$ alkoxy, provided that the compound has at least three rings.

2. A compound according to claim 1 wherein $R_3$ is H or —OH.

3. A compound according to claim 1 which is p-(naphthyl-1-methoxy)phenol.

4. A compound according to claim 1 which is p-(naphthyl-2-methoxy)phenol.

5. A compound according to claim 1 which is 2-(naphthyl-1-methyl)hydroquinone.

6. A compound according to claim 1 which is 2-(naphthyl-1-methyl)-1,4-benzoquinone.

7. A compound according to claim 1 which is o-xylylene-bis-hydroquinone ether.

8. A compound according to claim 1 which is m-xylylene-bis-hydroquinone ether.

9. A compound according to claim 1 which is p-xylylene-bis-hydroquinone ether.

10. A compound according to claim 1 which is hydroquinone(4-phenoxymethyl)benzyl ether.

11. A compound according to claim 1 which is 2,5-dibenzylhydroquinone.

12. A compound according to claim 1 which is 2,5-dibenzyl-1,4-benzoquinone.

13. A compound according to claim 1 which is 2,5-bis(naphthyl-1-methyl)hydroquinone.

14. A compound according to claim 1 which is 4-benzyloxy-2-benzylphenol.

15. A compound according to claim 1 which is 3-(naphthyl-1-methyl)-1,2-benzoquinone.

16. A compound according to claim 1 which is 1-(3,4-dihydroxybenzyl)naphthalene.

17. A compound according to claim 1 which is 2,6-di-t-butyl-4-(naphthyl-1-methoxy)phenol.

18. A composition comprising at least one monomer having a vinylic bond, containing dissolved therein an amount, effective to inhibit polymerization of said monomer, of a compound having the formula (1) or (2):

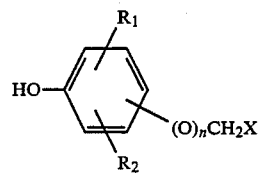

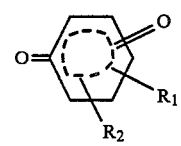

wherein
n is 0 or 1;
$R_1$ and $R_2$ are independently H, —OH, $C_1$–$C_6$ alkyl, -continued

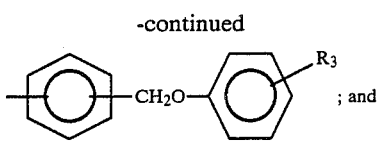; and

R$_3$ is H, —OH, —COO—(C$_1$–C$_6$ alkyl), C$_1$–C$_6$ alkyl, or C$_1$–C$_6$ alkoxy, provided that the inhibitor has at least three rings.

19. A composition according to claim 18 wherein the monomer is a monofunctional or multifunctional acrylic monomer.

20. A composition according to claim 18 wherein the polymerization inhibitor is p-(naphthyl-1-methoxy)-phenol.

21. A composition according to claim 18 wherein the polymerization inhibitor is p-(naphthyl-2-methoxy)-phenol.

22. A composition according to claim 18 wherein the polymerization inhibitor is 2-(naphthyl-1-methoxy)hydroquinone.

23. A composition according to claim 18 wherein the polymerization inhibitor is 2-(naphthyl-1-methoxy)benzoquinone.

24. A composition according to claim 18 wherein the polymerization inhibitor is o-xylylene-bis-hydroquinone ether.

25. A composition according to claim 18 wherein the polymerization inhibitor is m-xylylene-bis-hydroquinone ether.

26. A composition according to claim 18 wherein the polymerization inhibitor is p-xylylene-bis-hydroquinone ether.

27. A composition according to claim 18 wherein the polymerization inhibitor is hydroquinone(4-phenoxymethyl)benzyl ether.

28. A composition according to claim 18 wherein the polymerization inhibitor is 2,5-dibenzylhydroquinone.

29. A composition according to claim 18 wherein the polymerization inhibitor is 2,5-dibenzyl-1,4-benzoquinone.

30. A composition according to claim 18 wherein the polymerization inhibitor is 2,5-bis(naphthyl-1-methyl)-hydroquinone.

31. A composition according to claim 18 wherein the polymerization inhibitor is 4-benzyloxy-2-benzylphenol.

32. A composition according to claim 18 wherein the polymerization inhibitor is 3-(naphthyl-1-methyl)-1,2-benzoquinone.

33. A composition according to claim 18 wherein the polymerization inhibitor is 1-(3,4-dihydroxybenzyl)-naphthalene.

34. A composition according to claim 18 wherein the polymerization inhibitor is 2,6-di-t-butyl-4-(naphthyl-1-methoxy)phenol.

* * * * *